US010245583B1

(12) United States Patent
Snell et al.

(10) Patent No.: US 10,245,583 B1
(45) Date of Patent: Apr. 2, 2019

(54) USE OF CHARGE-CONTAINING MOLECULES LINKED WITH COVALENT BONDS TO ENHANCE ACETYLENE HYDROGENATION CATALYSTS

(71) Applicant: Chevron Phillips Chemical Company LP, The Woodlands, TX (US)

(72) Inventors: Ryan W. Snell, Jubail Industrial (SA); Zongxuan Hong, Houston, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 22 days.

(21) Appl. No.: 15/702,413

(22) Filed: Sep. 12, 2017

(51) Int. Cl.
| | | |
|---|---|---|
| *B01J 23/44* | (2006.01) | |
| *B01J 21/04* | (2006.01) | |
| *B01J 21/06* | (2006.01) | |
| *B01J 31/02* | (2006.01) | |
| *C07C 7/167* | (2006.01) | |
| *B01J 31/28* | (2006.01) | |

(Continued)

(52) U.S. Cl.
CPC ........... *B01J 31/0267* (2013.01); *B01J 31/28* (2013.01); *B01J 37/024* (2013.01); *B01J 37/16* (2013.01); *C07C 7/167* (2013.01); *B01J 2231/645* (2013.01)

(58) Field of Classification Search
CPC .. B01L 31/0208; B01L 31/0267; B01L 31/28; B01L 37/024; B01L 37/16; B01L 2231/645
USPC ................................. 502/150, 330, 333, 339
See application file for complete search history.

(56) References Cited

U.S. PATENT DOCUMENTS

| | | |
|---|---|---|
| 3,426,090 A | 2/1969 | Fishel et al. |
| 3,576,865 A | 4/1971 | Fleming et al. |
| 3,644,486 A | 2/1972 | Boldt et al. |

(Continued)

OTHER PUBLICATIONS

Schobert, R., et al., "Compounds with Two Carbon-Heteroatom Bonds. Heteroatom analogues of aldehydes and ketones," Science of Synthesis Category 4, 2004, Padwa Editor, Publishing Information & Table of Contents, pp. 973-974, vol. 27, Thieme.

(Continued)

*Primary Examiner* — Patricia L. Hailey
(74) *Attorney, Agent, or Firm* — Conley Rose, P.C.

(57) ABSTRACT

A composition containing a supported hydrogenation catalyst comprising palladium and a support, wherein the supported hydrogenation catalyst is capable of selectively hydrogenating highly unsaturated hydrocarbons to unsaturated hydrocarbons, and a dopant, wherein the dopant comprises at least one component selected from zwitterions, ylides, betaines, or combinations thereof. A method of making a selective hydrogenation catalyst by contacting a support with a palladium-containing compound to form a supported-palladium composition, contacting the supported-palladium composition with a dopant to form a selective hydrogenation catalyst precursor, wherein the dopant comprises at least one component selected from zwitterions, ylides, betaines, or combinations thereof, and reducing the selective hydrogenation catalyst precursor to form the selective hydrogenation catalyst. A selective hydrogenation catalyst produced via the method of making a selective hydrogenation catalyst, and a method of selectively hydrogenating highly unsaturated hydrocarbons to an unsaturated hydrocarbon enriched composition are also provided.

32 Claims, 3 Drawing Sheets

(51) Int. Cl.
    *B01J 37/02*     (2006.01)
    *B01J 37/16*     (2006.01)

(56) References Cited

U.S. PATENT DOCUMENTS

| | | | |
|---|---|---|---|
| 3,814,770 | A | 6/1974 | Andrews et al. |
| 4,404,124 | A | 9/1983 | Johnson et al. |
| 4,415,714 | A | 11/1983 | Mack |
| 4,484,015 | A | 11/1984 | Johnson et al. |
| 4,493,904 | A | 1/1985 | Mack |
| 6,319,428 | B1 * | 11/2001 | Michot ............... B01J 31/0215 252/500 |
| 9,181,356 | B2 | 11/2015 | Hsieh et al. |
| 9,346,719 | B2 | 5/2016 | Shih et al. |
| 2004/0037770 | A1 | 2/2004 | Fischer et al. |
| 2004/0106798 | A1 | 6/2004 | Bremer et al. |
| 2006/0217579 | A1 | 9/2006 | Bailey |
| 2007/0114155 | A1 | 5/2007 | Cholley et al. |
| 2011/0065950 | A1 | 3/2011 | Riisager et al. |
| 2013/0102819 | A1 | 4/2013 | Szesni et al. |

OTHER PUBLICATIONS

Periodic Table of Elements, Feb. 4, 1985, C&EN, p. 27.

UOP Method 578-02, "Automated Pore Volume and Pore Size Distribution of Porous Substances by Mercury Porosimetry," UOP LLC, 1984, pp. 1-14.

Zhou et al., Ionic Liquid and Plasma Effects on SiO2 Supported Pd for Selective Hydrogenation of Acetylene. Catalysis Today, 2013, vol. 211, pp. 147-155, Elsevier B.V.

Filing receipt and specification for patent application entitled "Use of Organic Dopants to Enhance Acetylene Hydrogenation Catalysts," by Ryan W. Snell, et al., filed Sep. 12, 2017 as U.S. Appl. No. 15/702,411.

Office Action dated Jun. 19, 2018 (20 pages), U.S. Appl. No. 15/702,411, filed Sep. 12, 2017.

Zhu et al., "'Unsymmetric' palladium(II) complexes with ligand 4',5'-diaza-9'-(4,5-disubstituted-1,3-dithiole-2-ylidene)-fluorene," Inorganica Chimica Acta, 2003, vol. 351, pp. 177-182, Elsevier B.V.

* cited by examiner

USE OF CHARGE-CONTAINING MOLECULES LINKED WITH COVALENT BONDS TO ENHANCE ACETYLENE HYDROGENATION CATALYSTS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Technical Field

The present disclosure relates to the production of unsaturated hydrocarbons, and more particularly to a selective hydrogenation catalyst and methods of making and using same.

Background

Unsaturated hydrocarbons such as ethylene and propylene are often employed as feedstocks in preparing value-added chemicals and polymers. Unsaturated hydrocarbons can be produced by pyrolysis or steam cracking of hydrocarbons including hydrocarbons derived from coal, hydrocarbons derived from synthetic crude, naphthas, refinery gases, ethane, propane, butane, and the like. Unsaturated hydrocarbons produced in these manners can contain small proportions of highly unsaturated hydrocarbons such as acetylenes and diolefins that can adversely affect the production of subsequent chemicals and polymers. Thus, to form an unsaturated hydrocarbon product, such as a polymer grade monoolefin, the amount of acetylenes and diolefins in the monoolefin stream is typically reduced. For example, in polymer grade ethylene, the acetylene content typically is less than about 2 ppmw.

One technique commonly used to reduce the amount of acetylenes and diolefins in an unsaturated hydrocarbon stream comprising primarily monoolefins involves selectively hydrogenating the acetylenes and diolefins to monoolefins. This process is selective in that hydrogenation of the monoolefin and the highly unsaturated hydrocarbons to saturated hydrocarbons is minimized. For example, the hydrogenation of ethylene or acetylene to ethane is minimized.

One challenge to the selective hydrogenation process is the potential for runaway reactions that lead to the uncontrollable reduction of unsaturated monoolefin (e.g., ethylene) to saturated hydrocarbon (e.g., ethane). One methodology to minimize runaway reactions is to increase the amount of selectivity enhancers in the hydrogenation catalyst. Thus, catalyst preparations may comprise one or more selectivity enhancers. Selectivity enhancers are materials, such as alkali metal halides, that increase the catalyst selectivity for the hydrogenation of highly unsaturated olefins to unsaturated olefins. The use of additional amounts of selectivity enhancers, also termed increased loadings, may lead to improved catalyst selectivity; however, the increased loadings may have drawbacks such as decreased catalyst activity.

One way to evaluate a selective hydrogenation catalyst is the operating window, which is the difference between two different determined temperature points, T1 and T2. T1 is the "clean-up" temperature, which can be defined to be the temperature at which a highly unsaturated hydrocarbon in the feed has been converted such that there is less than 20 ppmw in the product. T2 is the "runaway" temperature, defined to be where over hydrogenation has occurred to the point that ethane makes up 3 wt. % of the product. The larger the operating window, the more selective the catalyst is, and the less likely there is for unwanted runaway.

Therefore, a need exists for a selective hydrogenation catalyst that displays improved performance, such as an improved operating window and/or a desired selectivity and/or activity.

SUMMARY

Disclosed herein is a composition comprising: a supported hydrogenation catalyst comprising palladium and a support, wherein the supported hydrogenation catalyst is capable of selectively hydrogenating highly unsaturated hydrocarbons to unsaturated hydrocarbons; and a dopant, wherein the dopant comprises at least one component selected from zwitterions, ylides, betaines, or combinations thereof.

Also disclosed herein is a method of making a selective hydrogenation catalyst, the method comprising: contacting a support with a palladium-containing compound to form a supported-palladium composition; contacting the supported-palladium composition with a dopant to form a selective hydrogenation catalyst precursor, wherein the dopant comprises at least one component selected from zwitterions, ylides, betaines, or combinations thereof; and reducing the selective hydrogenation catalyst precursor to form the selective hydrogenation catalyst.

Also disclosed herein is a selective hydrogenation catalyst prepared by contacting a support with a palladium-containing compound to form a supported-palladium composition; contacting the supported-palladium composition with a dopant to form a selective hydrogenation catalyst precursor, wherein the dopant comprises at least one component selected from zwitterions, ylides, betaines, or combinations thereof; and reducing the selective hydrogenation catalyst precursor to form the selective hydrogenation catalyst.

Also disclosed herein is a method of selectively hydrogenating highly unsaturated hydrocarbons to an unsaturated hydrocarbon enriched composition, the method comprising: contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises at least one component selected from zwitterions, ylides, betaines, or combinations thereof.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

DETAILED DESCRIPTION

Figure 1:
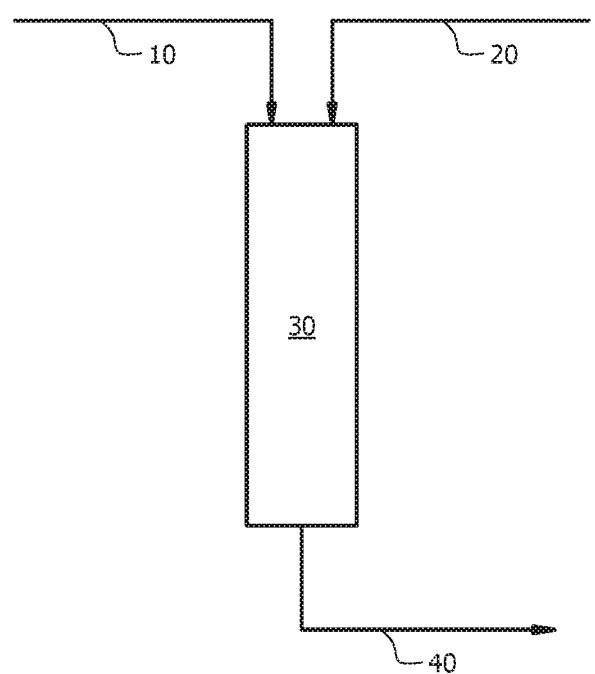
FIG. 1 is a process flow diagram of an embodiment of a selective hydrogenation process.

Selective hydrogenation catalysts typically comprise supported Pd/Ag. The addition of selectivity enhancers, such as KF, to a palladium-based catalyst can improve the operating window thereof. Furthermore, the addition of ionic liquids to catalysts may provide catalysts having improvements in hydrogenation performance. Both KF and the ionic liquids are salts that do not contain covalent bonds between the positive and negative charges. It has been unexpectedly discovered that single molecules containing both positive and negative charges linked through covalent bond(s) can be beneficial dopants for selective hydrogenation catalysts (e.g., palladium-based acetylene hydrogenation catalysts).

It should be understood at the outset that although an illustrative implementation of one or more embodiments is provided below, the disclosed systems and/or methods can be implemented using any number of techniques, whether currently known or in existence. The disclosure should in no way be limited to the illustrative implementations, drawings, and techniques illustrated below, including the exemplary designs and implementations illustrated and described herein, but can be modified within the scope of the appended claims along with their full scope of equivalents.

In an embodiment, a method of making a selective hydrogenation catalyst comprises contacting an inorganic catalyst support with a palladium-containing compound to form a supported-palladium composition and contacting the supported-palladium composition with a dopant. Herein, the disclosure will focus on the use of dopants comprising both positive and negative charges in a single molecule, the positively and negatively charged portions linked via covalent bond(s). In an embodiment, the methodologies disclosed herein result in selective hydrogenation catalysts having enhanced selectivity, improved operating windows, and/or improved recovery from deactivation by sulfur. Catalysts of the type disclosed herein can be utilized as selective hydrogenation catalysts (SHC).

It is to be understood that the SHC is the result of contacting the components disclosed herein (e.g., inorganic support, palladium, dopant, etc.) to form a composition that can be utilized as a selective hydrogenation catalyst. The materials as utilized to form the SHC can contact and be converted such that the original material is not discernible as a separate entity in the SHC. For example, the disclosure will describe utilization of a dopant and a metal-containing compound in the formation of the SHC. The SHC utilized as a selective hydrogenation catalyst can contain one or more components of the dopant or the metal-containing compound; however, the dopant or the metal-containing compound as originally contacted with the other components of the SHC may not be discernible in the final product.

The SHC can be used for selectively hydrogenating highly unsaturated hydrocarbons to unsaturated hydrocarbons. As used herein, a highly unsaturated hydrocarbon is defined as a hydrocarbon containing a triple bond, two conjugated carbon-carbon double bonds, or two cumulative carbon-carbon double bonds. As used herein, an unsaturated hydrocarbon is defined as a hydrocarbon containing an isolated carbon-carbon double bond. Examples of highly unsaturated hydrocarbons include, without limitation, acetylene, methylacetylene, and propadiene. Examples of unsaturated hydrocarbons include ethylene and propylene. It is also understood that the term "catalyst" refers to the support together with the materials impregnated in or on the support.

In an embodiment, the SHC can comprise an inorganic support such as, for example and without limitation, aluminas, silicas, titanias, zirconias, aluminosilicates (e.g., clays, ceramics, and/or zeolites), spinels (e.g., zinc aluminate, zinc titanate, and/or magnesium aluminate), or a combination thereof. In an embodiment, the SHC comprises an alumina support. In some embodiments, the alumina support comprises an alpha ($\alpha$)-alumina support.

The inorganic support can have a surface area of from about 2 to about 100 square meters per gram ($m^2/g$), alternatively of from about 2 $m^2/g$ to about 75 $m^2/g$, alternatively of from about 3 $m^2/g$ to about 50 $m^2/g$, alternatively of from about 4 $m^2/g$ to about 25 $m^2/g$, or alternatively of from about 5 $m^2/g$ to about 15 $m^2/g$. The surface area of the support can be determined using any suitable method. An example of a suitable method includes the Brunauer, Emmett, and Teller ("BET") method, which measures the quantity of nitrogen adsorbed on the support. Alternatively, the surface area of the support can be measured by a mercury intrusion method such as is described in ASTM UOP 578-02, entitled "Automated Pore Volume and Pore Size Distribution of Porous Substances by MERCURY Porosimetry," which is hereby incorporated herein by reference in its entirety for all purposes not contrary to this disclosure.

Particles of the inorganic support generally have an average diameter of from about 1 mm to about 10 mm, alternatively from about 2 mm to about 6 mm, alternatively from about 2 mm to about 4 mm, alternatively from about 3 mm to about 5 mm, alternatively from about 3.8 mm to about 4.2 mm, or alternatively from about 4 mm to about 6 mm, and can have any suitable shape. In an embodiment, the shape of the inorganic support can be cylindrical. In an alternative embodiment, the shape of the inorganic support can be spherical. In an embodiment, the inorganic support can be present in an amount such that it comprises the balance of the SHC when all other components are accounted for.

In an embodiment, the SHC comprises a Group 10 metal. Groups of elements of the table are indicated using the numbering scheme indicated in the version of the periodic table of elements published in *Chemical and Engineering News*, 63(5), 27, 1985. In an embodiment, the metals can comprise nickel, palladium, platinum, or combinations thereof. In an embodiment, the metal comprises palladium. Palladium can be added to the SHC by contacting the inorganic support with a palladium-containing compound to form a supported-palladium composition as will be described in more detail later herein. Examples of suitable palladium-containing compounds include, without limitation, palladium chloride, palladium nitrate, ammonium hexachloropalladate, ammonium tetrachloropalladate, palladium acetate, palladium bromide, palladium iodide, tetraamminepalladium nitrate, or combinations thereof. In an embodiment, the palladium-containing compound is a component of an aqueous solution. An example of a palladium-containing solution suitable for use in this disclosure includes, without limitation, a solution comprising palladium metal.

In an embodiment, the SHC can be prepared using a palladium-containing compound in an amount of from about 0.005 wt. % to about 5 wt. % based on the total weight of the SHC, alternatively from about 0.01 wt. % to about 3 wt. %, alternatively from about 0.02 wt. % to about 1 wt. %, alternatively from about 0.02 wt. % to about 0.04 wt. %, alternatively from about 0.018 wt. % to about 0.05 wt. %, or alternatively from about 0.03 wt. % to about 0.05 wt. %. The amount of palladium incorporated into the SHC can be in the range described herein for the amount of palladium-containing compound used to prepare the SHC.

In an embodiment, the SHC comprises a dopant. In embodiments, the dopant comprises a single molecule containing both positive and negative charges linked through covalent bond(s). The positive and negative charges may exist only in certain pH ranges and/or as part of resonance structures. In embodiments, the dopant comprises a zwitterion, also sometimes referred to as a dipolar ion or inner salt, which is a neutral molecule comprising both positive and negative electrical charges. In embodiments, the zwitterion comprises multiple positive and negative charges. In embodiments, the zwitterion comprises carbonyl imides, azomethine imides, vinyl carbenes, ylides, betaines or a combination thereof.

In embodiments, the dopant comprises a betaine, which is a neutral compound comprising a positively charged cationic functional group comprising an onium ion which bears no hydrogen atom, and a negatively charged functional group, such as a carboxylate group. The onium ion may be the result of protonation of a mononuclear parent hydride of a pnictogen (Group 15 of the Periodic Table of the Elements), a chalcogen (Group 16), or a halogen (Group 17). In embodiments, the onium ion is derived from a pnictogen (e.g., a quaternary ammonium or phosphonium cation).

In embodiments, the dopant is selected from ylides, or neutral (1,2-) dipolar molecules comprising a negatively charged atom directly attached to a heteroatom with a formal positive charge (e.g., nitrogen, phosphorus, or sulfur. In embodiments, the dopant is a ylide compound comprising phosphorus, also referred to as a phosphorus ylide. In embodiments, the dopant is selected from phosphorus ylides (or alkylidene phosphoranes), having the formula $R^1_3P\!=\!CHR^2$. The stability, reactivity, and selectivity of phosphorus ylides depend on the residue $R^2$ attached to the ylidic α-carbon atom and also, to a minor extent, on the substituent $R^1$ bonded to the phosphorus. In embodiments, the dopant comprises a 'stabilized' ylide, a 'semistabilized' or 'moderated' ylide, or a 'nonstabilized' or 'reactive' ylide, as described in *Science of Synthesis: Compounds with Two Carbon-Heteroatom Bonds,* 2004, Padwa Editor, pp. 973-974, which is hereby incorporated herein by reference for all purposes not contrary to this disclosure.

In embodiments, the dopant is a 'stabilized' ylide, wherein $R^2$ comprises COX or CN. In embodiments, the dopant comprises a 'semistabilized' or 'moderated' ylide, wherein $R^2$ is aryl or allyl. In embodiments, the dopant is a 'nonstabilized' ylide, wherein $R^2$ is H or alkyl. In embodiments, $R^2$ comprises a carbonyl group. In embodiments, $R^2$ comprises COX, and X is selected from hydrogen; hydrocarbyl groups; $-OR^3$ wherein $R^3$ is hydrogen, or a hydrocarbyl group. In embodiments, $R^3$ comprises an alkyl, or aryl group. In embodiments, $R^2$ does not comprise a sulfonyl group. In embodiments, each $R^1$ may be independently selected from alkyl or aryl groups. In embodiments, each $R^1$ may be independently selected from methyl and phenyl groups.

Upon reading this disclosure, one of skill in the art will recognize suitable dopants, and an exhaustive list of such will not be provided herein. By way of non-limiting examples, in embodiments, a dopant according to this disclosure comprises a phosphoranylidene. In embodiments, the dopant is selected from 1-(triphenyl phosphoranylidene)-2-propanone (TPP-2P), 2-(triphenylphosphoranlyidene) propionaldehyde, (triphenylphosphoranylidene) acetonitrile, (triphenylphosphoranlyidene)acetaldehyde, (triphenyl phosphoranlyidene)ketene, ethyl(triphenylphosphoranylidene)pyruvate, (phenacylidene) triphenyl phosphorane, or a combination thereof.

For purposes of this application, the term "hydrocarbyl(s)" or "hydrocarbyl group(s)" as used herein in accordance with the definition specified by IUPAC: a univalent group or groups derived by the removal of one hydrogen atom from a carbon atom of a "hydrocarbon." A hydrocarbyl group can be an aliphatic, inclusive of acyclic and cyclic groups. A hydrocarbyl group can include rings, ring systems, aromatic rings, and aromatic ring systems. Hydrocarbyl groups can include, by way of example, aryl, alkyl, cycloalkyl, and combinations of these groups, among others. Hydrocarbyl groups can be linear or branched unless otherwise specified. For the purposes of this application, the terms "alkyl," or "cycloalkyl" refer to a univalent group derived by removal of a hydrogen atom from any carbon atom of an alkane. For example, in embodiments, the hydrocarbyl comprises a methyl group. For the purposes of this application, the terms "aryl," or "arylene" refers to a univalent group derived by removal of a hydrogen atom from any carbon atom of an aryl ring. For example, in embodiments, the hydrocarbyl comprises a phenyl group, a benzyl group, a substituted phenyl group, a substituted benzyl group, or a combination thereof.

A dopant suitable for use in this disclosure can be further characterized by a boiling point of greater than or equal to about 200° C., 250° C., or 300° C. at atmospheric pressure. In embodiments, the dopant is thermally stable, and has a boiling point that is sufficiently high that the dopant doesn't desorb immediately from the catalyst surface during selective hydrogenation. In other embodiments, the dopant is converted into a species having a boiling point of greater than or equal to about 200° C., 250° C., or 300° C. at atmospheric pressure upon exposure to moisture and/or air.

In an embodiment, the dopant can be present in the mixture for the preparation of the SHC in an amount of from about 0.001 wt. % to about 5 wt. % based on the weight of the dopant to the total weight of the SHC, alternatively from about 0.005 wt. % to about 5 wt. %, alternatively from about 0.001 wt. % to about 3 wt. %, or alternatively from about 0.005 wt. % to about 2 wt. %. In an embodiment, the dopant can be present in the mixture for the preparation of the SHC in an amount of less than or equal to about 5, 4, 3, 2, 1, or 0.5 wt. %. The amount of dopant incorporated into the SHC can be in the range described herein for the amount of dopant used to prepare the SHC.

In an embodiment, the SHC can further comprise one or more selectivity enhancers. Suitable selectivity enhancers include, but are not limited to, Group 1B metals, Group 1B metal compounds, silver compounds, gold compounds, fluorine, fluoride compounds, metals, alkali metal compounds, alkaline metals, alkaline metal compounds, iodine, iodide compounds, or combinations thereof. In an embodiment, the SHC comprises one or more selectivity enhancers which can be present in the mixture for preparation of the SHC in an amount of from about 0.001 wt. % to about 10 wt. % based on the total weight of the SHC, alternatively from about 0.01 wt. % to about 5 wt. %, alternatively from about 0.005 wt.

% to about 5 wt. %, alternatively from about 0.01 wt. % to about 2 wt. %. The amount of selectivity enhancer incorporated into the SHC can be in the range described herein for the amount of selectivity enhancer used to prepare the SHC.

In an embodiment, the selectivity enhancer comprises silver (Ag), silver compounds, or combinations thereof. Examples of suitable silver compounds include, without limitation, silver nitrate, silver acetate, silver bromide, silver chloride, silver iodide, silver fluoride, or combinations thereof. In an embodiment, the selectivity enhancer comprises silver nitrate. The SHC can be prepared using silver nitrate in an amount of from about 0.005 wt. % to about 5 wt. % silver based on the total weight of the SHC, alternatively from about 0.01 wt. % to about 1 wt. % silver, alternatively from about 0.02 wt. % to about 0.5 wt. %, alternatively from about 0.03 wt. % to about 0.3 wt. %. The amount of silver incorporated into the SHC can be in the range described herein for the amount of silver nitrate used to prepare the SHC.

In an embodiment, the selectivity enhancer comprises alkali metals, alkali metal compounds, or combinations thereof. Examples of suitable alkali metal compounds include, without limitation, elemental alkali metal, alkali metal halides (e.g., alkali metal fluoride, alkali metal chloride, alkali metal bromide, alkali metal iodide), alkali metal oxides, alkali metal carbonate, alkali metal sulfate, alkali metal phosphate, alkali metal borate, or combinations thereof. In an embodiment, the selectivity enhancer comprises potassium fluoride (KF). In another embodiment, the SHC can be prepared using an alkali metal compound in an amount of from about 0.01 wt. % to about 5 wt. % based on the total weight of the SHC, alternatively from about 0.05 wt. % to about 2 wt. %, alternatively from about 0.05 wt. % to about 1 wt. %. The amount of alkali metal incorporated into the SHC can be in the range described herein for the amount of alkali metal compound used to prepare the SHC.

Although described hereinbelow with reference to a supported palladium composition and potassium fluoride and/or silver as optional selectivity enhancer(s) (e.g., supported Pd/KF, supported Pd/Ag, or supported Pd/KF/Ag), SHCs of this disclosure may be formed with any metal, support, and selectivity enhancer(s) described hereinabove, in combination with a dopant according to this disclosure.

In an embodiment, a method of preparing a SHC can initiate with the contacting of an inorganic support with a palladium-containing compound to form a supported-palladium composition. The contacting can be carried out using any suitable technique. For example, the inorganic support can be contacted with a solution containing the palladium-containing compound by soaking in a volume of solution containing the palladium-containing compound that is greater than the pore volume of the support. In such embodiments, the resulting supported-palladium composition can have greater than about 90 wt. %, alternatively from about 92 wt. % to about 98 wt. %, alternatively from about 94 wt. % to about 96 wt. % of the palladium concentrated near the periphery of the supported-palladium composition, as to form a palladium skin.

The palladium skin can be any thickness as long as such skin thickness can promote the hydrogenation processes disclosed herein. Generally, the thickness of the palladium skin can be in the range of from about 1 micron to about 3000 microns, alternatively from about 5 microns to about 2000 microns, alternatively from about 10 microns to about 1000 microns, alternatively from about 50 microns to about 500 microns. Examples of such methods are further described in more details in U.S. Pat. Nos. 4,404,124 and 4,484,015, each of which is hereby incorporated herein by reference in its entirety for all purposes not contrary to this disclosure.

Any suitable method can be used for determining the thickness of the palladium skin of the supported-palladium composition, selective hydrogenation catalyst and/or SHC composition. For example, one method involves breaking open a representative sample of the SHC and treating the catalyst pieces with a dilute alcoholic solution of N,N-dimethyl-para-nitrosoaniline. The treating solution can react with the palladium to give a red color that can be used to evaluate the distribution of the palladium on the catalyst. Yet another technique for measuring the concentration of the palladium in the skin of the SHC involves breaking open a representative sample of catalyst, followed by treating the catalyst pieces with a reducing agent such as hydrogen to change the color of the skin and thereby evaluate the distribution of the palladium. Alternatively, the palladium skin thickness can be determined by analyzing a cross-section of the catalyst using an electron microprobe analyzer.

The supported-palladium composition formed by contacting the inorganic support with a solution of a palladium-containing compound can optionally be dried at a temperature of from about 15° C. to about 150° C., alternatively from about 30° C. to about 100° C., or alternatively from about 60° C. to about 100° C.; and for a period of from about 0.1 hour to about 100 hours, alternatively from about 0.5 hour to about 20 hours, or alternatively from about 1 hour to about 10 hours. Alternatively or additionally, the supported-palladium composition can be calcined. This calcining step can be carried out at temperatures up to about 850° C., alternatively of from about 150° C. to about 700° C., alternatively from about 150° C. to about 600° C., or alternatively from about 150° C. to about 550° C.; and for a period of from about 0.2 hour to about 20 hours, alternatively from about 0.5 hour to about 20 hours, or alternatively from about 1 hour to about 10 hours. In an embodiment, the supported-palladium composition can be dried and subsequently calcined.

In an embodiment, a method of preparing a SHC further comprises contacting the supported-palladium composition with a dopant of the type described herein (e.g., a phosphorus ylide or a composition, e.g., solution, comprising same).

In an embodiment, the dopant is contacted with the supported-palladium composition. The contacting can be carried out in any suitable manner that will yield a selective hydrogenation catalyst meeting the parameters described herein; such as for example by incipient wetness impregnation. Herein a SHC is formed by the contacting of a supported-palladium composition with a dopant is designated as a Pd/D. Briefly, the dopant can be dissolved in a solvent to form a dopant-containing solution. The solvent can be any suitable solvent in which the dopant dissolves. In embodiments, the solvent comprises water. In embodiments, the solvent comprises an organic solvent selected from toluene, benzene, acetone, dimethyl sulfoxide (DMSO), carbon tetrachloride, and the like. In embodiments, the solvent comprises organic alcohols such as butanol, ethanol, or methanol. Desirably, the solvent has a boiling point below 150° C. and can easily be removed by drying at the temperatures described in this application. The dopant may be combined with the solvent in an amount of from about 0.01 wt. % to about 3 wt. %, from about 0.05 wt. % to about 2.5 wt. %, or from about 0.1 wt. % to about 2 wt. %. In an embodiment, the supported-palladium composition can be added to or combined with the dopant solution to form the Pd/D composition.

In an embodiment, silver can be added to the supported-palladium composition (without a dopant). For example, the supported-palladium composition can be placed in an aqueous silver nitrate solution of a quantity greater than that necessary to fill the pore volume of the composition. The resulting material can be a supported palladium/silver composition (herein this particular embodiment is referred to as a Pd/Ag composition).

In an embodiment, the Pd/Ag composition is further contacted with a dopant. The contacting can be carried out as described above, to form a Pd/Ag/D.

In an embodiment, one or more alkali metals can be added to the Pd/Ag composition (prior to or following contacting with a dopant) using any suitable technique such as those described previously herein. In an embodiment, the selectivity enhancer comprises an alkali fluoride, and the resulting material is a palladium/silver/alkali metal fluoride supported composition. In an embodiment, the selectivity enhancer comprises potassium fluoride, and the resulting material is a palladium/silver/potassium fluoride (Pd/Ag/KF) supported composition.

In an embodiment, the supported-palladium composition is contacted with both an alkali metal halide and a silver compound (prior to or following contacting with a dopant). Contacting of the supported-palladium composition with both an alkali metal halide and a silver compound can be carried out simultaneously; alternatively, the contacting can be carried out sequentially in any user-desired order.

In an embodiment, one or more selectivity enhancers can be contacted with the supported-palladium composition prior to contacting the composition with a dopant. In such embodiments, the resulting composition (e.g., comprising Pd/Ag, Pd/KF, or Pd/Ag/KF) can be calcined under the conditions described previously herein, and subsequently contacted with a dopant. For example, a dopant can be added to the Pd/Ag, Pd/KF, and/or Pd/Ag/KF composition to provide Pd/Ag/D, Pd/KF/D, and/or Pd/Ag/KF/D compositions, respectively. In an alternative embodiment, one or more selectivity enhancers can be contacted with the supported-palladium composition following contacting of the composition with a dopant. For example, Ag and/or KF can be added to the Pd/D composition to provide Pd/Ag/D, Pd/KF/D, and/or Pd/Ag/KF/D compositions. In yet another alternative embodiment, one or more selectivity enhancers can be contacted with the supported-palladium composition, and dopant simultaneously.

In an embodiment, a method of preparing a SHC of the type disclosed herein comprises contacting an α-alumina support, palladium, and a dopant, each of the type previously disclosed herein. In an alternative embodiment, a method of preparing a SHC of the type disclosed herein comprises contacting an α-alumina support, palladium, a dopant, and one or more selectivity enhancers, (e.g., silver and/or potassium fluoride). The resultant materials (Pd/D, Pd/Ag/D, Pd/KF/D, and/or Pd/Ag/KF/D compositions) can be dried to form a dried catalyst composition. In some embodiments, this drying step can be carried out at a temperature in the range of from about 0° C. to about 150° C., alternatively from about 30° C. to about 100° C., alternatively from about 50° C. to about 80° C.; and for a period of from about 0.1 hour to about 100 hours, alternatively from about 0.5 hour to about 20 hours, or alternatively from about 1 hour to about 10 hours at pressures ranging from ambient to 100 torr of vacuum. In an embodiment, a dopant precursor is employed so that upon exposure to air, moisture and/or the temperature ranges used during drying of the aforementioned composition the precursor dopant is converted to a dopant of the type described herein, or a dopant as described herein changes form during drying or other pre-hydrogenation step, whereby the SHC comprises an altered form of the added dopant. In some embodiments, this drying step can be carried out at ambient pressure, alternatively, this drying step can be carried out at a pressure from about 0.1 atm to 1 atm.

The dried catalyst composition can be reduced using hydrogen gas or a hydrogen gas containing feed, e.g., the feed stream of the selective hydrogenation process, thereby providing for optimum operation of the selective hydrogenation process to form a SHC. Such a gaseous hydrogen reduction can be carried out at a temperature in the range of from, for example, about 0° C. to about 150° C., alternatively about 20° C. to about 100° C., or alternatively about 25° C. to about 80° C.

In an embodiment, a method of preparing a SHC comprises contacting an inorganic support with a palladium-containing compound (e.g., palladium chloride, palladium nitrate) to form a supported-palladium composition; and drying and calcining the supported-palladium composition to form a dried and calcined supported-palladium composition. The dried and calcined supported-palladium composition can then be contacted with a silver-containing compound (e.g., silver nitrite, silver fluoride) to form a Pd/Ag composition, which can then be dried and/or calcined to form a dried and/or calcined Pd/Ag composition. The dried and/or calcined Pd/Ag composition can be contacted with an alkali metal fluoride (e.g., potassium fluoride) to form a Pd/Ag/KF composition that is then dried and calcined. The dried and calcined Pd/Ag/KF composition can then be contacted with a dopant to form a catalyst composition that is subsequently reduced to form a SHC.

In some embodiments, the SHC can be formed from a palladium/silver/alkali metal salt composition that has been contacted with a dopant. In some embodiments, the resultant material is a catalyst precursor that can be further treated to form a SHC. In some embodiments, further treatments comprise drying. In some embodiments, further treatments comprise reducing. In some embodiments, further treatments comprise drying and reducing.

In an embodiment, the SHC catalyzes a selective hydrogenation process. In such processes, the SHC can be contacted with an unsaturated hydrocarbon stream primarily containing unsaturated hydrocarbons, e.g., ethylene, but also containing a highly unsaturated hydrocarbon, e.g., acetylene. The contacting can be executed in the presence of hydrogen at conditions effective to selectively hydrogenate the highly unsaturated hydrocarbon to an unsaturated hydrocarbon. In an embodiment, SHCs of the type disclosed herein are used in the hydrogenation of highly unsaturated hydrocarbons such as, for example and without limitation, acetylene, methylacetylene, propadiene, butadiene or combinations thereof.

FIG. 1 illustrates an embodiment of a hydrogenation process that utilizes a SHC of the type disclosed herein. The hydrogenation process includes feeding an unsaturated hydrocarbon stream 10 and a hydrogen ($H_2$) stream 20 to a hydrogenation reactor 30 within which the SHC is disposed. The unsaturated hydrocarbon stream 10 primarily comprises one or more unsaturated hydrocarbons, but it can also contain one or more highly unsaturated hydrocarbons such as, for example and without limitation, acetylene, methylacetylene, propadiene, and butadiene. Alternatively, unsaturated hydrocarbon stream 10 and hydrogen stream 20 can be combined in a single stream that is fed to hydrogenation reactor 30.

In an embodiment, reactor 30 is a selective hydrogenation reactor that can belong to an acetylene removal unit of an unsaturated hydrocarbon production plant in a backend configuration. As used herein, "backend" refers to the location of the acetylene removal unit in an unsaturated hydrocarbon production unit that receives a lower boiling fraction from a deethanizer fractionation tower. The deethanizer tower receives a higher boiling fraction from a demethanizer fractionation tower. The demethanizer tower receives a feed from an unsaturated hydrocarbon production process.

In an embodiment, reactor 30 is a selective hydrogenation reactor that can belong to an acetylene removal unit of an unsaturated hydrocarbon production plant in a frontend deethanizer configuration. As used herein, "frontend deethanizer" refers to the location of the acetylene removal unit in an unsaturated hydrocarbon production unit that receives a lower boiling fraction from a deethanizer fractionation tower. The deethanizer tower receives a feed from an unsaturated hydrocarbon production process.

In an embodiment, reactor 30 is a selective hydrogenation reactor that can belong to an acetylene removal unit of an unsaturated hydrocarbon production plant in a frontend depropanizer configuration. As used herein, "frontend depropanizer" refers to the location of the acetylene removal unit in an unsaturated hydrocarbon production unit that receives the lower boiling fraction from a depropanizer fractionation tower. The depropanizer tower receives a feed from an unsaturated hydrocarbon production process.

In an embodiment, reactor 30 is a selective hydrogenation reactor that can belong to an acetylene removal unit of an unsaturated hydrocarbon production plant in a raw gas configuration. As used herein, "raw gas" refers to the location of the acetylene removal unit in an unsaturated hydrocarbon production unit that receives a feed from an unsaturated hydrocarbon production process without any intervening hydrocarbon fractionation.

It is understood that hydrogenation reactor 30, and likewise the selective hydrogenation catalysts disclosed herein, are not limited to use in backend acetylene removal units, frontend deethanizer units, frontend depropanizer, or raw gas units and can be used in any process wherein a highly unsaturated hydrocarbons contained within an unsaturated hydrocarbon stream is selectively hydrogenated to a unsaturated hydrocarbon.

In those embodiments wherein the acetylene removal unit is in a backend configuration, the highly unsaturated hydrocarbon being fed to hydrogenation reactor 30 comprises acetylene. The mole ratio of the hydrogen to the acetylene being fed to hydrogenation reactor 30 can be in the range of from about 0.1 to about 10, alternatively from about 0.2 to about 5, alternatively from about 0.5 to about 3.

In embodiments wherein the acetylene removal unit is in a front-end deethanizer, front-end depropanizer or raw gas configuration, the highly unsaturated hydrocarbon being fed to the hydrogenation reactor 30 comprises acetylene. In such an embodiment, the mole ratio of the hydrogen to the acetylene being fed to the hydrogenation reactor 30 can be in the range of from about 10 to about 3000, alternatively from about 10 to about 2000, alternatively from about 10 to about 1500.

In embodiments wherein the acetylene removal unit is in a front-end depropanizer or raw gas configuration, the highly unsaturated hydrocarbon being fed to hydrogenation reactor 30 comprises methylacetylene. In such an embodiment, the mole ratio of the hydrogen to the methylacetylene being fed to hydrogenation reactor 30 can be in the range of from about 3 to about 3000, alternatively from about 5 to about 2000, alternatively from about 10 to about 1500.

In embodiments wherein the acetylene removal unit is in a front-end depropanizer or raw gas configuration, the highly unsaturated hydrocarbon being fed to hydrogenation reactor 30 comprises propadiene. In such an embodiment, the mole ratio of the hydrogen to the propadiene being fed to hydrogenation reactor 30 can be in the range of from about 3 to about 3000, alternatively from about 5 to about 2000, alternatively from about 10 to about 1500.

In another embodiment, reactor 30 can represent a plurality of reactors. The plurality of reactors can optionally be separated by a means to remove heat produced by the reaction. The plurality of reactors can optionally be separated by a means to control inlet and effluent flows from reactors or heat removal means allowing for individual or alternatively groups of reactors within the plurality of reactors to be regenerated. The selective hydrogenation catalyst can be arranged in any suitable configuration within hydrogenation reactor 30, such as a fixed catalyst bed.

Carbon monoxide can also be fed to reactor 30 via a separate stream (not shown), or it can be combined with hydrogen stream 20. In an embodiment, the amount of carbon monoxide being fed to reactor 30 during the hydrogenation process is less than about 0.15 mol % based on the total moles of fluid being fed to reactor 30.

Hydrogenation reactor 30 can be operated at conditions effective for selective hydrogenation of the highly unsaturated hydrocarbons to one or more unsaturated hydrocarbons upon contacting the selective hydrogenation catalyst in the presence of the hydrogen. The conditions are desirably effective to maximize hydrogenation of highly unsaturated hydrocarbons to unsaturated hydrocarbons and to minimize hydrogenation of highly unsaturated hydrocarbons and unsaturated hydrocarbons to saturated hydrocarbons. In some embodiments, acetylene can be selectively hydrogenated to ethylene. Alternatively, methylacetylene can be selectively hydrogenated to propylene. Alternatively, propadiene can be selectively hydrogenated to propylene. Alternatively, butadiene can be selectively hydrogenated to butenes. In some embodiments, the temperature within the hydrogenation zone can be in the range of from about 5° C. to about 300° C., alternatively from about 10° C. to about 250° C., alternatively from about 15° C. to about 200° C. In some embodiments, the pressure within the hydrogenation zone can be in the range of from about 15 (204 kPa) to about 2,000 (13,890 kPa) pounds per square inch gauge (psig), alternatively from about 50 psig (446 kPa) to about 1,500 psig (10,443 kPa), alternatively from about 100 psig (790 kPa) to about 1,000 psig (6,996 kPa).

Referring back to FIG. 1, an effluent stream 40 comprising unsaturated hydrocarbons, including the one or more monoolefins produced in hydrogenation reactor 30, and any unconverted reactants exit hydrogenation reactor 30. In an embodiment, effluent stream 40 primarily comprises ethylene and/or comprises less than about 5 ppmw, alternatively less than about 1 ppmw of highly unsaturated hydrocarbons.

In an embodiment, a SHC of the type described herein can have a comparable catalytic activity when compared to an otherwise similar selective hydrogenation catalyst prepared in the absence of a dopant (e.g., compared to an SHC comprising Pd/Ag, Pd/KF, or Pd/Ag/KF). The comparable catalytic activity can translate to a comparable clean up temperature. Herein, the clean-up temperature is designated T1 and refers to the temperature at which the concentration of highly unsaturated hydrocarbon (e.g., acetylene) concentration drops below 20 ppmw in a feed stream comprising unsaturated hydrocarbon and highly unsaturated hydrocarbons such as acetylene and diolefins. In an embodiment, a SHC of the type disclosed herein can have a T1 of from about 80° F. to about 160° F., alternatively from about 85° F. to about 145° F., alternatively from about 90° F. to about 130° F.

In an embodiment, a SHC can exhibit an increased selectivity when compared to an otherwise similar SHC prepared in the absence of a dopant (e.g., compared to an SHC comprising Pd/Ag, Pd/KF, or Pd/Ag/KF). Herein selectivity refers to a comparison between the rate at which the SHC converts a highly unsaturated hydrocarbon to an unsaturated hydrocarbon, herein termed Conversion 1, and the rate at which the SHC converts an unsaturated hydrocarbon to a saturated hydrocarbon, herein termed Conversion 2. A SHC can display an increased rate of Conversion 1 and a decreased rate of Conversion 2 when compared to an otherwise similar catalyst prepared in the absence of a dopant of the type described herein. Conversion 2 is highly exothermic and can lead to runaway reactions or the uncontrollable conversion of unsaturated hydrocarbons to saturated hydrocarbons due to the presence of excess unsaturated hydrocarbons. The higher selectivity of the SHC can, in embodiments, result in a reduction in the incidence of runaway reactions and increase the operating window of the hydrogenation process.

In embodiments, the highly unsaturated hydrocarbons comprise acetylene, and the operating window is at least about 10° F., 20° F., or 35° F. greater than a method utilizing an otherwise similar composition prepared with a catalyst lacking the dopant (e.g., compared to an SHC comprising Pd/Ag, Pd/KF, or Pd/Ag/KF).

An operating window ($\Delta T$) is defined as the difference between a runaway temperature (T2) at which 3 wt. % of saturated hydrocarbon (e.g., ethane) is found in the product of a reaction having a feedstock comprising highly unsaturated and unsaturated hydrocarbons, and the clean-up temperature (T1). $\Delta T$ is a convenient measure of the operational stability of a selective hydrogenation catalyst for the hydrogenation of highly unsaturated hydrocarbons (e.g., acetylene) to unsaturated hydrocarbons (e.g., ethylene). The more stable a hydrogenation catalyst, the higher the temperature beyond T1 required to hydrogenate a given unsaturated hydrocarbon (e.g., ethylene). The T2 is coincident with the temperature at which a high probability exists for a runaway ethylene hydrogenation reaction to occur in an adiabatic reactor. Therefore, a larger $\Delta T$ translates to a more stable catalyst and a wider operation window for the complete acetylene hydrogenation.

In an embodiment, a SHC of the type disclosed herein can have an operating window of from about 25° F. to about 180° F., alternatively from about 30° F. to about 170° F., or alternatively from about 35° F. to about 160° F. In an embodiment, a SHC of the type disclosed herein can have an operating window of greater than or equal to about 60° F., 70° F., or 75° F. The operating window of a SHC of the type described herein can be increased by greater than about 20%, alternatively greater than about 25%, alternatively greater than about 30%, or alternatively greater than about 35% when compared to an otherwise similar catalyst prepared in the absence of a dopant (e.g., compared to an SHC comprising Pd/Ag, Pd/KF, or Pd/Ag/KF). A higher operating window indicates a more selective SHC. Selectivity typically refers to the percent ethylene conversion of acetylene at T1.

In embodiments, a SHC of this disclosure is desirable from an environmental health and safety standpoint. For example, a dopant as described herein may be less volatile than other dopants known in the art. Utilization of a thermally stable dopant as described herein, may reduce concerns of a volatile dopant remaining in the unsaturated hydrocarbon (e.g., ethylene) product. In embodiments, a dopant as provided herein has a low toxicity. Such a low toxicity may be indicated by an NFPA 704 Health Rating of less than or equal to 2, 1, or 0.

In an embodiment, a SHC can display activity comparable to or greater than an otherwise similar SHC prepared in the absence of a dopant (e.g., compared to an SHC comprising Pd/Ag, Pd/KF, or Pd/Ag/KF). In an embodiment, a SHC can display a more constant activity relative to an otherwise similar SHC prepared in the absence of a dopant (e.g., compared to an SHC comprising Pd/Ag, Pd/KF, or Pd/Ag/KF). In an embodiment, a SHC a comprising a supported-palladium catalyst composition with a dopant of the type described herein (e.g., Pd/D) can result in the catalyst displaying a selectivity and activity comparable to that of a hydrogenation catalyst comprising one or more selectivity enhancers (e.g., compared to Pd/Ag, Pd/KF, or Pd/Ag/KF). In another embodiment, treatment of a hydrogenation catalyst comprising a single selectivity enhancer with a dopant of the type described herein (e.g., Pd/Ag/D or Pd/KF/D) can result in the catalyst displaying a selectivity and activity comparable to that of a hydrogenation catalyst comprising at least two selectivity enhancers (e.g., Pd/Ag/KF). As a SHC according to this disclosure may comprise fewer (or no) additional selectivity enhancers, thus requiring fewer steps in the manufacture thereof, in embodiments, utilization of a dopant(s) according to this disclosure (e.g., the ylide of Example 2 hereinbelow) could enable lower cost replacement of such selectivity enhancer(s) (e.g., Ag and KF of Example 2).

A method for the selective hydrogenation of a hydrocarbon feed comprising highly unsaturated and unsaturated hydrocarbons can comprise the preparation of a SHC catalyst comprising a dopant of the type disclosed herein having a boiling point below a maximum temperature attained during selective hydrogenation and contacting of the SHC with the hydrocarbon feed in a reactor having an initial temperature (T0). The dopant can remain associated with the SHC upon start of the reaction at T0. Depending on the boiling point of the dopant, over time if the temperature increases above the boiling point of the dopant, the dopant can be evaporated (i.e., boiled off) from the SHC. The SHC prepared utilizing the dopant can display an increased activity over time and an enhanced initial selectivity when the dopant is associated or has been associated with the SHC. This can be advantageous for reactions employing a fresh catalyst as a SHC prepared utilizing the dopant can allow for a more stable operation and a reduction in the potential for a runaway reaction due to the increase in catalyst selectivity and predictable catalytic activity as the composition stabilizes. In other words, the presence of the SHC prepared utilizing the dopant can aid in the control of the reaction during start up following a catalyst change out. Following the loss of the dopant, the resulting composition can display an activity and selectivity comparable to that of an otherwise similar catalyst prepared in the absence of a dopant (e.g., an SHC comprising Pd/Ag, Pd/KF, or Pd/Ag/KF).

In an alternative embodiment, a method for the selective hydrogenation of a hydrocarbon feed comprising highly unsaturated and unsaturated hydrocarbons comprises the preparation of a SHC comprising a high boiling point dopant (i.e., having a boiling point above a maximum temperature attained during selective hydrogenation), as described previously herein, and contacting of the SHC with the hydrocarbon feed. The high boiling point dopant compound can remain associated with the SHC throughout the lifetime of the catalyst providing the reaction temperature remains below the boiling point of the high boiling point dopant. The SHC prepared utilizing the high boiling point dopant can display improvements in characteristics such as catalytic activity and selectivity when compared to an otherwise similar catalyst composition prepared in the absence of a dopant (e.g., compared to an SHC comprising Pd/Ag, Pd/KF, or Pd/Ag/KF).

In an alternative embodiment, a method for the selective hydrogenation of a hydrocarbon feed comprising highly unsaturated and unsaturated hydrocarbons comprises the preparation of a SHC comprising a high boiling point dopant, and a low boiling point dopant, each of the type described previously herein, and contacting of the SHC with the hydrocarbon feed. The SHC prepared utilizing both the low boiling point dopant, and the high boiling point dopant can display improvements in characteristics such as catalytic activity and selectivity when compared to an otherwise similar catalyst composition prepared in the absence of a dopant (e.g., compared to an SHC comprising Pd/Ag, Pd/KF, or Pd/Ag/KF). Further, these SHCs comprising one or more dopants can be advantageous for reactions employing a fresh catalyst as such SHCs can allow for a more stable operation and a reduction in the potential for runaway reactions due to the increase in catalyst selectivity and predictable catalytic activity as the composition stabilizes.

EXAMPLES

The disclosure having been generally described, the following examples are given as particular embodiments of the disclosure and to demonstrate the practice and advantages thereof. It is understood that the examples are given by way of illustration and are not intended to limit the specification or the claims to follow in any manner.

Example 1: Comparison of Pd/Ag/KF and Pd/Ag/KF/D Catalysts

To study the effect of an SHC according to this disclosure, a Pd/Ag/KF/D catalyst according to this disclosure comprising 1 wt. % TPP-2P as dopant was studied. Resonance structures for the stable phosphorus ylide, TPP-2P, are shown in (1) below.

(1)

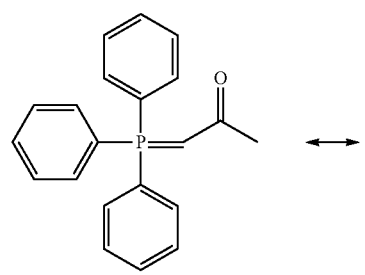

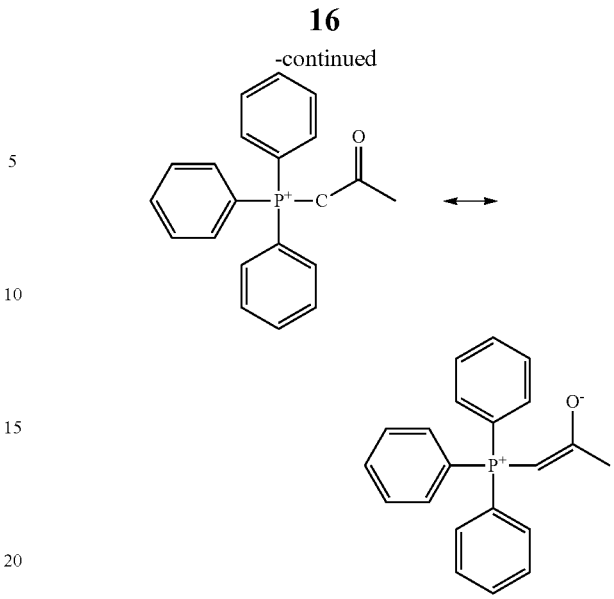

A comparative or 'baseline' Pd/Ag/KF catalyst, CC1, was prepared using a commercial Pd/Ag/KF catalyst/α-Al$_2$O$_3$ pellets supplied by Süd Chemie of Huefeld, Germany, in the form of 4 mm×4 mm tablets as described in U.S. Pat. No. 4,484,015, which is hereby incorporated herein by reference in its entirety for all purposes not contrary to this disclosure. The α-Al$_2$O$_3$ pellets had a surface area of about 5 to about 7 m$^2$/g (determined by the BET method employing N$_2$ adsorption).

More specifically, 100 g of alumina support was impregnated with a solution of 100 g PdCl$_2$ solution with Pd concentration at 400 ppmw. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium. The above Pd/α-Al$_2$O$_3$ pellets were then impregnated with a solution of 100 g AgNO$_3$ solution with an Ag concentration of 410 ppmw. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium and 400 ppm by weight (ppmw) silver. The above catalyst was further impregnated by incipient wetness with a KF solution with 0.149 g of KF dissolved in 26 g of water. This catalyst was then dried at 90° C. for 1 hour, at 200° C. for 1 hour, at 400° C. for 1 hour, and at 540° C. for 3 hours, resulting in a catalyst comprising 400 ppm by weight (ppmw) palladium, 400 ppm by weight (ppmw) silver and 1000 ppmw potassium.

A Pd/Ag/KF/D SHC according to this disclosure, SHC-1, comprising 1 wt. % TPP-2P was prepared by dissolving 1.0 g of TPP-2P into 30 mL of ethanol, and impregnating 100 g of the CC1 catalyst composition with the TPP-2P containing solution. The impregnated catalyst was then allowed to sit open in a hood overnight to dry.

Twenty (20) mL of catalyst was then loaded into a reactor and reduced for 60 minutes at 100° F. in 200 mL/min H$_2$ and 200 psig. The catalyst was then used to hydrogenate an acetylene-containing gas mixture. The synthetic feed used in these examples is typical of a feed from the top of a deethanizer fractionation tower in an ethylene plant, with the exception that ethane was replaced with methane in the synthetic feed so that any ethane found in the reactor effluent was the result of the hydrogenation of ethylene. The synthetic feed contained approximately 25.8 mole percent methane, 47.4 mole percent ethylene, 0.16 mole percent acetylene, 26.6 mole percent hydrogen, 0.034 mole percent carbon monoxide.

Figure 2:
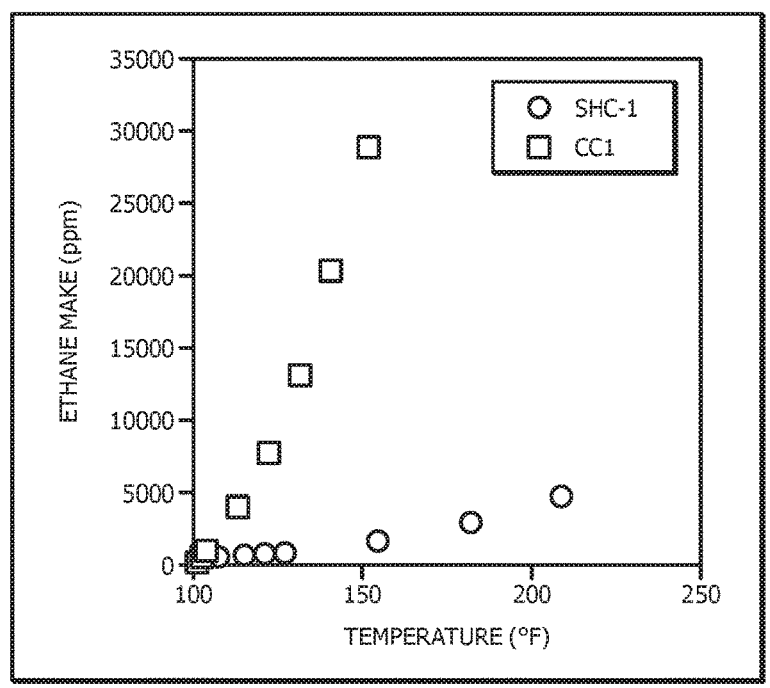
FIG. 2 is a plot of ethane make as a function of temperature for the catalysts of Example 1.
Figure 3:
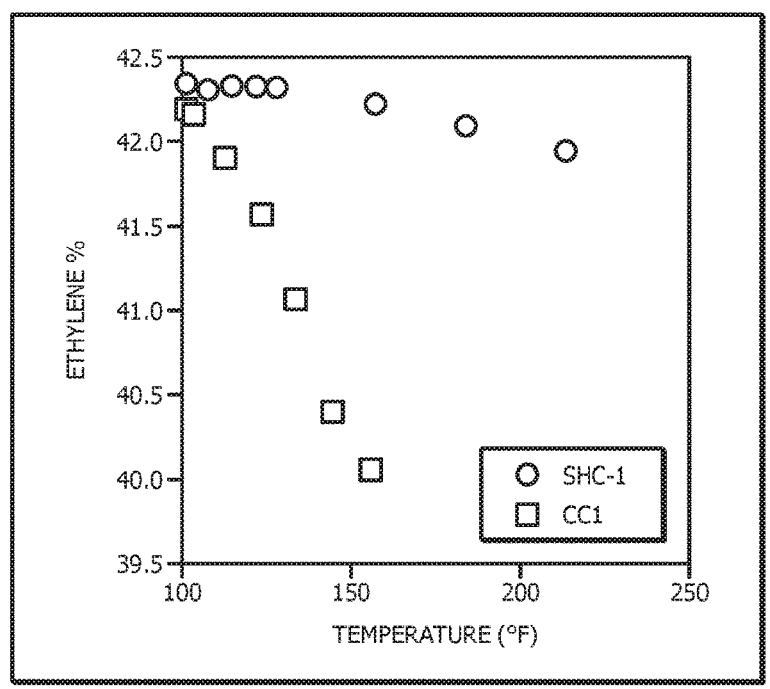
FIG. 3 is a plot of the weight percent of ethylene as a function of temperature for the catalysts of Example 1.

Results of this TPP-2P containing catalyst, SHC-1, along with the baseline CC1 catalyst are shown below in FIGS. 2 and 3 and Table 1. FIG. 2 is a plot of ethane make (ppm) as a function of temperature (° F.) for the CC1 and SHC-1 catalysts. FIG. 3 is a plot of weight percent ethylene as a function of temperature (° F.) for the CC1 and SHC-1 catalysts. The TPP-2P containing SHC-1 catalyst is more selective (i.e., increased weight percent ethylene) than the comparative CC1 catalyst and has a larger operating window than the comparative catalyst CC1. The activity of TPP-2P catalyst SHC-1 was lower than that of the CC1 catalyst, as indicated by the higher T1 value. Without limitation, reduced loading of dopant may provide a SHC having increased activity, while maintaining an enhanced operating window.

TABLE 1

Pd/Ag/KF and Pd/Ag/KF/D Catalyst Performance from Example 1

|  | CC1 (Pd/Ag/KF) | SHC-1 (Pd/Ag/KF/D) |
| --- | --- | --- |
| T1 (° F.) | 103 | 130 |
| T2 (° F.) | 159 | >211* |
| Operating Window (° F.) | 56 | >80 |

*211° F. was the highest temperature obtained during the test and this was not sufficient to hit T2.

Example 2: Comparison of Pd/Ag/KF and Pd/D Catalysts

Decreasing the number of manufacturing steps for making a SHC is desirable, as multiple steps (e.g., the addition of multiple stability enhancers such as, without limitation, silver and potassium fluoride) can add significant cost to the final catalyst. Palladium-only selective hydrogenation catalysts tend to be too active and unselective, leading to the addition of various selectivity enhancers, such as Ag and KF, which improve the operating window. To study the possible use of a dopant according to this disclosure in place of, rather than in addition to, other selectivity enhancer(s), a Pd/D catalyst, SHC-2, comprising 0.5 weight percent TPP-2P as dopant was studied. The Pd/D SHC according to this disclosure, SHC-2, was prepared by dissolving 0.5 g of TPP-2P into 30 mL of ethanol, and impregnating 100 g of a Pd catalyst composition with the TPP-2P containing solution. The impregnated catalyst was then allowed to sit open in a hood overnight to dry. The SHC-2 catalyst was reduced and utilized to hydrogenate an acetylene-containing gas mixture, as described in Example 1.

Figure 4:
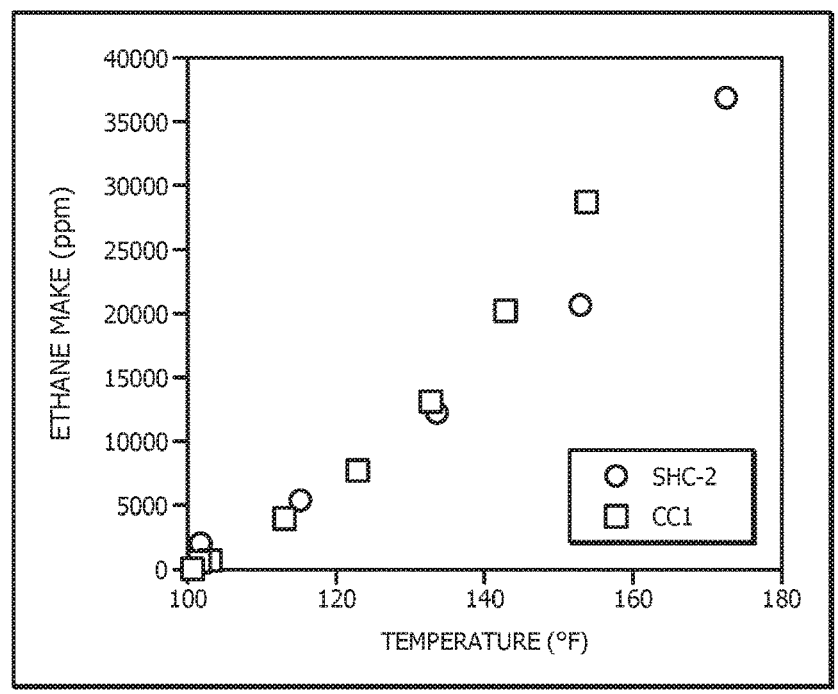
FIG. 4 is a plot of ethane make as a function of temperature for the catalysts of Example 2.
Figure 5:
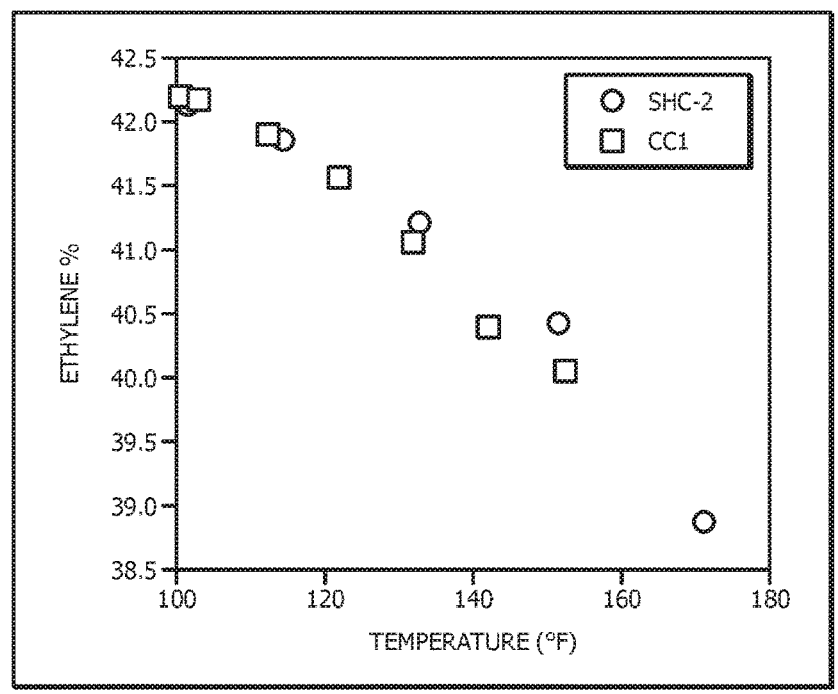
FIG. 5 is a plot of the weight percent of ethylene as a function of temperature for the catalysts of Example 2.

Results of this TPP-2P containing catalyst, SHC-2, along with the baseline CC1 catalyst of Example 1 are shown below in FIGS. 4 and 5 and Table 2. FIG. 4 is a plot of ethane make (ppm) as a function of temperature (° F.) for the CC1 and SHC-2 catalysts. FIG. 5 is a plot of weight percent ethylene as a function of temperature (° F.) for the CC1 and SHC-2 catalysts. The TPP-2P containing SHC-2 catalyst performed equivalently or better (e.g., with respect to selectivity and operating window) than the comparative CC1 catalyst, which contained Pd/Ag/KF. The SHC-2 catalyst had an operating window 34% greater than the comparative CC1 catalyst. Additionally the starting activity is comparable to the CC1 catalyst as well.

TABLE 2

Pd/Ag/KF and Pd/D Catalyst Performance from Example 2

|  | CC1 (Pd/Ag/KF) | SHC-2 (Pd/D) |
| --- | --- | --- |
| T1 (° F.) | 103 | 96 |
| T2 (° F.) | 159 | 171 |
| Operating Window (° F.) | 56 | 75 |

Additional Embodiments

The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Alternative embodiments that result from combining, integrating, and/or omitting features of the embodiment(s) are also within the scope of the disclosure. While compositions and methods are described in broader terms of "having", "comprising," "containing," or "including" various components or steps, the compositions and methods can also "consist essentially of" or "consist of" the various components and steps. Use of the term "optionally" with respect to any element of a claim means that the element is required, or alternatively, the element is not required, both alternatives being within the scope of the claim.

Numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents, the definitions that are consistent with this specification should be adopted.

The following are nonlimiting, specific embodiments in accordance with the present disclosure:

A: A composition comprising: a supported hydrogenation catalyst comprising palladium and a support, wherein the supported hydrogenation catalyst is capable of selectively hydrogenating highly unsaturated hydrocarbons to unsaturated hydrocarbons; and a dopant, wherein the dopant comprises at least one component selected from zwitterions, ylides, betaines, or combinations thereof.

B: A method of making a selective hydrogenation catalyst, the method comprising: contacting a support with a palladium-containing compound to form a supported-palladium composition; contacting the supported-palladium composition with a dopant to form a selective hydrogenation catalyst precursor, wherein the dopant comprises at least one component selected from zwitterions, ylides, betaines, or combinations thereof; and reducing the selective hydrogenation catalyst precursor to form the selective hydrogenation catalyst.

C: A selective hydrogenation catalyst prepared by contacting a support with a palladium-containing compound to form a supported-palladium composition; contacting the supported-palladium composition with a dopant to form a selective hydrogenation catalyst precursor, wherein the dopant comprises at least one component selected from zwitterions, ylides, betaines, or combinations thereof; and reducing the selective hydrogenation catalyst precursor to form the selective hydrogenation catalyst.

D: A method of selectively hydrogenating highly unsaturated hydrocarbons to an unsaturated hydrocarbon enriched composition, the method comprising: contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises at least one component selected from zwitterions, ylides, betaines, or combinations thereof.

Each of embodiments A, B, C, and D may have one or more of the following additional elements: Element 1: wherein the dopant is selected from ylides. Element 2: wherein the dopant is selected from phosphorus ylides. Element 3: wherein the dopant is selected from phosphorus ylides further comprising a carbonyl group. Element 4: wherein the ylide is classified as stabilized and of the form $R^1_3$—P=$CHR^2$, wherein $R^2$ comprises a COX group or a CN group. Element 5: wherein the ylide is a phosphoranylidine selected from 1-(triphenylphosphoranylidene)-2-propanone (TPP-2P), 2-(Triphenylphosphoranlyidene)propionaldehyde, (triphenylphosphoranylidene)acetonitrile, (triphenylphosphoranlyidene)acetaldehyde, (triphenylphosphoranlyidene)ketene, (phenacylidene)triphenylphosphorane, ethyl(triphenylphosphoranylidene)pyruvate, or a combination thereof. Element 6: wherein the dopant has a boiling point of greater than or equal to about 200° C. Element 7: further comprising at least one component selected from Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, or combinations thereof disposed on the support. Element 8: comprising an inorganic support. Element 9: wherein the palladium is present in an amount of from about 0.005 wt. % to about 5 wt. % Pd based on the total weight of the catalyst. Element 10: wherein the dopant is present in an amount of from about 0.005 wt. % to about 5 wt. % based on the total weight of the catalyst. Element 11: wherein the support has a surface area of from about 2 $m^2$/g to about 100 $m^2$/g, and wherein greater than about 90 wt. % of the palladium is concentrated near a periphery of the support. Element 12: wherein the support, the supported-palladium composition, the selective hydrogenation catalyst precursor, or the selective hydrogenation catalyst further comprises at least one component selected Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, or combinations thereof. Element 13: wherein the support is an inorganic support. Element 14: wherein the support comprises alpha alumina. Element 15: further comprising contacting the support, the supported-palladium composition, or the selective hydrogenation catalyst precursor with at least one selectivity enhancer. Element 16: wherein the at least one selectivity enhancer is selected from Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, or combinations thereof. Element 17: wherein the selectivity enhancer comprises elemental silver, silver nitrate, silver acetate, silver bromide, silver chloride, silver iodide, silver fluoride, or a combination thereof. Element 18: wherein the selectivity enhancer comprises elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or a combination thereof. Element 19: wherein the selectivity enhancer comprises silver and potassium fluoride. Element 20: wherein the selectivity enhancer is present in an amount of from about 0.005 wt. % to about 5 wt. % based on the total weight of the selective hydrogenation catalyst. Element 21: wherein the selectivity enhancer is present in an amount of from about 0.01 wt. % to about 5 wt. % based on the total weight of the selective hydrogenation catalyst. Element 22: further comprising drying the catalyst precursor at a temperature in the range of from about 0° C. to about 150° C. for a time period in the range of from about 0.1 hour to about 100 hours. Element 23: wherein the support comprises at least one component selected from aluminas, silicas, titanias, zirconias, aluminosilicates, spinels, or combinations thereof. Element 24: wherein the highly unsaturated hydrocarbons comprise at least one component selected from acetylene, methylacetylene, propadiene, butadiene, or combinations thereof. Element 25: wherein the conditions suitable for hydrogenation include conducting the step of contacting at a temperature less than about the boiling point of the dopant. Element 26: further comprising increasing the temperature to a temperature greater than or equal to about the boiling point of the dopant. Element 27: wherein the highly unsaturated hydrocarbon comprises acetylene, and wherein the selectivity to ethylene is at least about 20% greater than a method utilizing an otherwise similar composition prepared with a catalyst lacking the dopant.

While preferred embodiments of the invention have been shown and described, modifications thereof can be made by one skilled in the art without departing from the teachings of this disclosure. The embodiments described herein are exemplary only, and are not intended to be limiting. Many variations and modifications of the invention disclosed herein are possible and are within the scope of the invention.

Numerous other modifications, equivalents, and alternatives, will become apparent to those skilled in the art once the above disclosure is fully appreciated. It is intended that the following claims be interpreted to embrace all such modifications, equivalents, and alternatives where applicable. Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference, to the extent that they provide exemplary, procedural or other details supplementary to those set forth herein.

What is claimed is:

1. A composition comprising:
   a supported hydrogenation catalyst comprising palladium and an inorganic support selected from the group consisting of aluminas, silicas, titanias, zirconias, aluminosilicates, spinels, and combinations thereof, wherein the supported hydrogenation catalyst is capable of selectively hydrogenating highly unsaturated hydrocarbons to unsaturated hydrocarbons; and
   a dopant, wherein the dopant comprises at least one component selected from the group consisting of zwitterions, ylides, betaines, and combinations thereof.

2. The composition of claim 1, wherein the dopant is selected from ylides.

3. The composition of claim 2, wherein the dopant is selected from phosphorus ylides.

4. The composition of claim 3, wherein the dopant is selected from phosphorus ylides further comprising a carbonyl group.

5. The composition of claim 2, wherein the ylide is classified as stabilized and of the form $R^1_3$—P=$CHR^2$, wherein $R^2$ comprises a COX group or a CN group.

6. The composition of claim 5, wherein the ylide is a phosphoranylidine selected from the group consisting of 1-(triphenylphosphoranylidene)-2-propanone (TPP-2P), 2-(Triphenylphosphoranlyidene) propionaldehyde, (triphenylphosphoranylidene)acetonitrile, (triphenylphosphoranlyidene) acetaldehyde, (triphenylphosphoranylidene)ketene, (phenacylidene)triphenylphosphorane, ethyl(triphenylphosphoranylidene)pyruvate, and combinations thereof.

7. The composition of claim 1, wherein the dopant has a boiling point of greater than or equal to about 200° C.

8. The composition of claim 1 further comprising at least one selectivity enhancer selected from the group consisting of Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, and combinations thereof disposed on the inorganic support.

9. The composition of claim 1, wherein the palladium is present in an amount of from about 0.005 wt. % to about 5 wt. % based on the total weight of the catalyst.

10. The composition of claim 1, wherein the dopant is present in an amount of from about 0.005 wt. % to about 5 wt. % based on the total weight of the catalyst.

11. The composition of claim 1, wherein the inorganic support has a surface area of from about 2 m²/g to about 100 m²/g, and wherein greater than about 90 wt. % of the palladium is concentrated near a periphery of the inorganic support.

12. A method of making a selective hydrogenation catalyst, the method comprising:
   contacting an inorganic support selected from the group consisting of aluminas, silicas, titanias, zirconias, aluminosilicates, spinels, and combinations thereof with a palladium-containing compound to form a supported-palladium composition;
   contacting the supported-palladium composition with a dopant to form a selective hydrogenation catalyst precursor, wherein the dopant comprises at least one component selected from the group consisting of zwitterions, ylides, betaines, and combinations thereof; and
   reducing the selective hydrogenation catalyst precursor to form the selective hydrogenation catalyst.

13. The method of claim 12, wherein the dopant is selected from ylides.

14. The method of claim 13, wherein the dopant is selected from phosphorus ylides.

15. The method of claim 14, wherein the dopant is selected from phosphorus ylides further comprising a carbonyl group.

16. The method of claim 13, wherein the ylide is classified as stabilized and of the form $R^1_3$—P=$CHR^2$, wherein $R^2$ comprises a COX group or a CN group.

17. The method of claim 16, wherein ylide is a phosphoranylidine selected from the group consisting of 1-(triphenylphosphoranylidine)-2-propanone (TPP-2P), (triphenylphosphoranylidene) acetonitrile, (triphenylphosphoranlyidene)ketene, (phenacylidene)triphenylphosphorane, (triphenyl phosphoranlyidene)acetaldehyde, ethyl(triphenylphosphoranylidene)pyruvate, 2-(triphenyl phosphoranlyidene) propionaldehyde, and combinations thereof.

18. The method of claim 12, wherein the dopant has a boiling point of greater than or equal to about 200° C.

19. The method of claim 12, further comprising contacting the inorganic support, the supported-palladium composition, the selective hydrogenation catalyst precursor, or the selective hydrogenation catalyst with at least one selectivity enhancer selected from the group consisting of Group 1B metals, Group 1B metal compounds, silver compounds, fluorine, fluoride compounds, sulfur, sulfur compounds, alkali metal, alkali metal compounds, alkaline metals, alkaline metal compounds, iodine, iodide compounds, and combinations thereof.

20. The method of claim 19, wherein the selectivity enhancer comprises elemental silver, silver nitrate, silver acetate, silver bromide, silver chloride, silver iodide, silver fluoride, or a combination thereof.

21. The method of claim 19, wherein the selectivity enhancer comprises elemental alkali metal, alkali metal fluoride, alkali metal chloride, alkali metal bromide, alkali metal iodide, alkali metal oxide, alkali metal carbonate, alkali metal sulfate, alkali metal phosphate, alkali metal borate, potassium fluoride, or a combination thereof.

22. The method of claim 19, wherein the selectivity enhancer comprises silver and potassium fluoride.

23. The method of claim 19, wherein the selectivity enhancer is present in an amount of from about 0.005 wt. % to about 5 wt. % based on the total weight of the selective hydrogenation catalyst.

24. The method of claim 19, wherein contacting the inorganic support, the supported-palladium composition, the selective hydrogenation catalyst precursor, or the selective hydrogenation catalyst with the at least one selectivity enhancer comprises incipient wetness impregnation.

25. The method of claim 12, wherein the palladium is present in an amount of from about 0.005 wt. % to about 5 wt. % Pd based on the total weight of the selective hydrogenation catalyst.

26. The method of claim 12, wherein the dopant is present in an amount of from about 0.005 wt. % to about 5 wt. % based on the total weight of the selective hydrogenation catalyst.

27. A selective hydrogenation catalyst prepared according the method of claim 12.

28. The method of claim 12, wherein contacting the inorganic support with the palladium-containing compound to form the supported-palladium composition and contacting the supported-palladium composition with the dopant comprise incipient wetness impregnation.

29. A method of selectively hydrogenating highly unsaturated hydrocarbons to an unsaturated hydrocarbon enriched composition, the method comprising:
   contacting a supported catalyst comprising palladium and a dopant with a feed comprising highly unsaturated hydrocarbon under conditions suitable for hydrogenating at least a portion of the highly unsaturated hydrocarbon feed to form the unsaturated hydrocarbon enriched composition, wherein the dopant comprises at least one component selected from the group consisting of zwitterions, ylides, betaines, and combinations thereof.

30. The method of claim 29, wherein the highly unsaturated hydrocarbons comprise at least one component selected from the group consisting of acetylene, methylacetylene, propadiene, butadiene, and combinations thereof.

31. The method of claim 29, wherein the conditions suitable for hydrogenation include conducting the step of contacting at a temperature less than about the boiling point of the dopant.

32. The method of claim 31 further comprising increasing the temperature to a temperature greater than or equal to about the boiling point of the dopant.

* * * * *